United States Patent [19]

Ohnishi et al.

[11] Patent Number: 4,696,670
[45] Date of Patent: Sep. 29, 1987

[54] METHOD AND APPARATUS FOR TREATING BLOOD CONSTITUENTS

[75] Inventors: Michikazu Ohnishi, Kobe; Nobutaka Tani, Minoo, both of Japan

[73] Assignee: Kanegafuchi Kagaku Kogyo Kabushiki Kaisha, Osaka, Japan

[21] Appl. No.: 795,663

[22] Filed: Nov. 6, 1985

[30] Foreign Application Priority Data

Nov. 13, 1984 [JP] Japan .................. 59-240199

[51] Int. Cl.$^4$ .......................................... A61M 31/00
[52] U.S. Cl. ........................ 604/49; 210/340; 128/DIG. 3; 604/4
[58] Field of Search .......................... 604/4-6, 604/49, 51-53, 66, 403, 406, 7; 128/DIG. 3; 210/340, 341, 790, 927

[56] References Cited

U.S. PATENT DOCUMENTS

| | | | |
|---|---|---|---|
| 844,438 | 2/1907 | Bayley | 210/341 |
| 3,043,303 | 7/1962 | Still | 604/66 |
| 3,396,845 | 8/1968 | Bouskill | 210/341 |
| 3,585,995 | 6/1971 | Perkins | 604/4 |
| 3,896,733 | 7/1975 | Rosenburg | 604/4 |
| 4,014,329 | 3/1977 | Welch et al. | 604/406 |
| 4,401,430 | 8/1983 | Dorson, Jr. et al. | 604/4 |

Primary Examiner—C. Fred Rosenbaum
Assistant Examiner—Gene B. Kartchner
Attorney, Agent, or Firm—Wenderoth, Lind & Ponack

[57] ABSTRACT

A method for treating circulatory fluid constituents with an apparatus which includes a first switching device which connects the upstream side of a first circulatory fluid treatment device with a flow of circulatory fluid from a source, and a second switching device which connects the downstream side of the first circulatory fluid treatment device with a destination of the circulatory fluid. Next, the second switching device maintains the flow of circulatory fluid to the destination from the downstream side of the first circulatory fluid treatment device, the upstream side of the first circulatory fluid treatment device is disconnected with the flow of circulatory fluid from the source, and further a third switching device connects the upstream side of a second circulatory fluid treatment device to the flow of a circulatory fluid from the source, and a fourth switching device connects the downstream side of the second circulatory fluid treatment device to communicate with the upstream side of the first circulatory fluid treatment device. Finally, the third switching device maintains the flow of circulatory fluid from the source into the upstream side of the second circulatory fluid treatment device, the downstream side of the first circulatory fluid treatment device is disconnected from sending the flow of circulatory fluid to the destination, and a fifth switching device connects the downstream side of the second circulatory fluid treatment device with the destination for the flow of circulatory fluid thereto.

2 Claims, 10 Drawing Figures

METHOD AND APPARATUS FOR TREATING BLOOD CONSTITUENTS

BACKGROUND OF THE INVENTION

The present invention relates to a method and an apparatus for treating one or more constituents of the blood of a living patient, and more particularly relate to such a method and apparatus which are effective for minimizing the amount of blood removed from the patient for any great period of time as well as for minimizing the amount of physiological saline solution or the like which enters into the body of the patient.

In the present specification, the term "blood constituent" is used not only to refer to typical blood constituents such as red blood corpuscles, white blood corpuscles, blood platelets, and the like, and to liquid blood constituents such as blood plasma and the like, but also to refer to whole blood and to any portion thereof; and the term "treatment of a blood constituent" and similar terms not only are used to refer to administration of treatment to one or more such blood constituents in order for example to remove noxious or useless substances therefrom, to add medicine thereto, to replenish insufficient quantity thereof, or the like, but also are used to refer to application of such treatments as the supplying of a blood constituent or constituents, the replacing of a blood constituent or constituents with one or more other constituents, or the like.

Various illnesses can be cured or mitigated, or their symptoms may be relieved, by administering treatment of a constituent of the blood of the patient. According to the Japanese health insurance practice, six illnesses are regarded as being worthy of such blood constituent treatment from the point of view of payment of medical insurance costs, namely: drug intoxication, acute hepatitis, hyperglobulinemia, hyperlipemia, multiple myeloma, and myasthenia gravis. In addition to these illnesses detailed above, practical and valid instances of the application of such treatment to a large number of conditions such as rheumatoid arthritis, liver failure, erythematosus, and nephritis have been reported. The present invention is intended to promote the effectiveness of treatment for a variety of illnesses, including but not limited to those listed above.

Figure 5A:
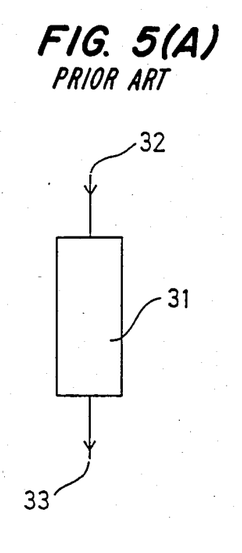
FIG. 5a is a schematic illustration of a prior art blood constituent treatment apparatus.

In the prior art, there are various per se known methods and apparatuses, employing adsorbent material or the like, which are currently used with the object of eliminating noxious components in the blood and so on. FIG. 5A of the accompanying drawings shows an exemplary one such apparatus in a schematic view. The principal portion of this apparatus comprises a blood collection portion 32 which is connected to the body of the patient so as to take out a flow of blood therefrom, a blood constituent treatment device 31 which performs some such processing on said flow of blood, and a blood return portion 33 which is connected to the body of the patient so as to return said flow of blood thereto. According to the particular requirements of each individual case, such an apparatus may further comprise various other components not particularly shown, such as a blood pump for maintaining proper blood volume, a blood pressure meter, a blood anticoagulant agent injecting device, a dripper chamber for eliminating air bubbles in the blood, a heater for maintaining an appropriate temperature for the blood while it is outside the body, and so on. Further, if a blood plasma separating device is provided with this apparatus, it is possible to supply the blood constituent treatment device 31 with blood plasma in separated form.

Now, for operating this apparatus, first a quantity of physiological saline solution or the like is pre-filled into the blood constituent treatment device 31, and then, according to the inflow of blood constituents which are to be treated, this physiological saline solution is pushed, by the patient's blood which is flowing out from his or her body via the blood collection portion 32 connected thereto, out of said blood constituent treatment device 31 in the downwards direction in the figure, so as to pass through the blood return portion 33 into the body of the patient while being replaced by said blood from above. And thereafter, after the blood constituent treatment device 31 has become filled up with blood, the blood of the patient continues to circulate through it and is appropriately treated by it, for example by being purified of noxious components contained therein.

Figure 5B:
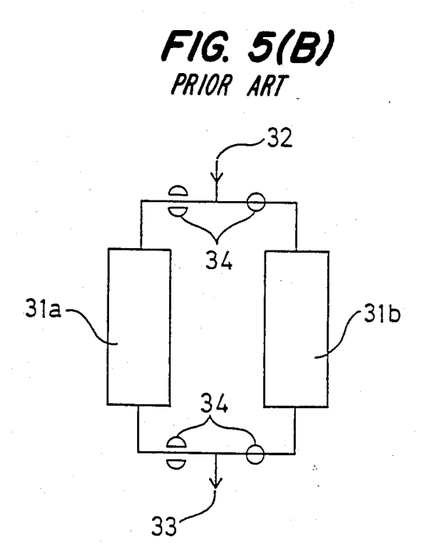
FIG. 5b is another schematic illustration of a prior art blood constituent treatment apparatus, which has two alternatively selectable parallel branches.

Further, as a refinement of such a prior art apparatus, in order to increase treatment capacity, there is a per se known type of prior art blood constituent treatment apparatus as shown in FIG. 5B of the accompanying drawings in a schematic view. In this apparatus, a plurality (two in the illustrated case) of first and second blood constituent treatment devices 31a and 31b are provided in parallel, and are used alternatively. Using conduit switching means including a plurality of switching devices 34, first the blood of the patient containing the constituent to be treated is circulated to the first blood constituent treatment device 31a, by the left pair of said switching devices 34 being opened while the right pair thereof is closed so that the left branch of the apparatus as seen in the figure is utilized. Thus, first the physiological saline solution initially charged into said first blood constituent treatment device 31a is driven out by the inflowing blood and is harmlessly injected into the body of the patient, and thereafter the inflowing blood is appropriately treated in said first blood constituent treatment device 31a. Then, when the processing capacity of said first blood constituent treatment device 31a has become exhausted or deteriorated, said left pair of said switching devices 34 is closed and said right pair thereof is opened. Thus, the apparatus is switched over to the right branch thereof, and first the physiological saline solution initially charged into the second blood constituent treatment device 31b is driven out by the inflowing blood and is harmlessly injected into the body of the patient, and thereafter the inflowing blood is again appropriately treated in said second blood constituent treatment device 31b. Thereby, the fresh processing capability of said second blood constituent treatment device 31b can be utilized.

Figure 5C:
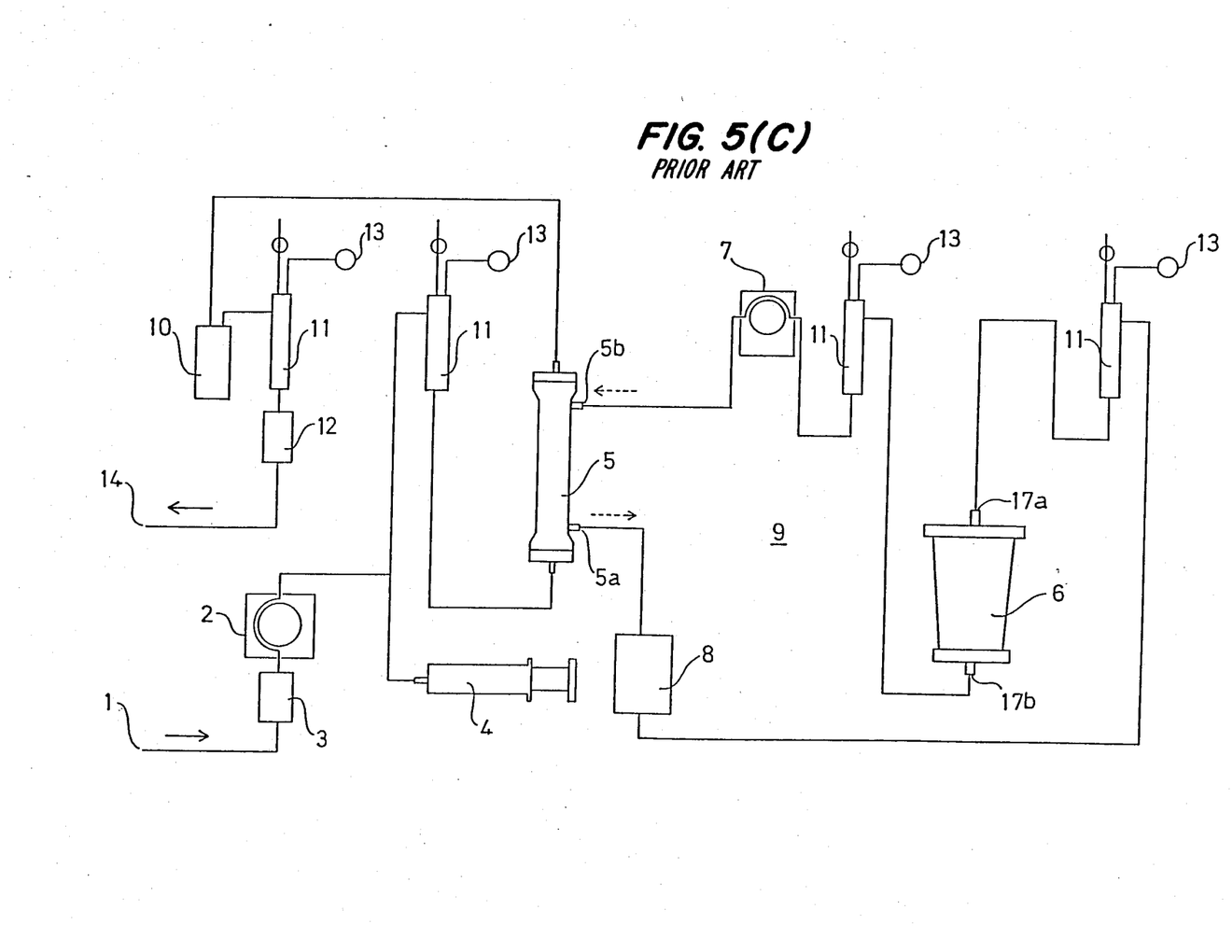
FIG. 5c is a schematic illustration of a practical example of another circuit configuration for another prior art blood constituent treatment apparatus.

In order to explain such prior art devices concretely, a practical example of a circuit configuration for treatment of the blood of a patient is shown in FIG. 5C of the accompanying drawings. This exemplary case is a circuit for removing low density and very low density lipoprotein (hereinafter referred to generically as LDL) from blood. Such LDL is considered to be the cause of hyperlipemia, as well as of high blood cholesterol level disease, arteriosclerosis, and the like.

In this exemplary prior art circuit configuration, shown in FIG. 5C there are comprised the following devices: a blood collection portion 1 which is connected to the body of the patient so as to remove a flow of blood therefrom; a blood pump 2 and a collected blood pressure irregularity alarm 3 for maintaining proper blood flow volume; a blood anticoagulant agent injecting device 4 for preventing the coagulation of the blood as it traverses this circuit; a blood plasma separator/combiner device 5 which has the twin functions of (a) separating out blood plasma from the blood passing into it, keeping the blood corpuscles in said blood behind while dispatching said plasma to its plasma side, and (b) remixing together said blood corpuscles and said blood plasma, after said blood plasma has been treated; a blood plasma constituent treatment circuit 9 connected to said blood plasma separator/combiner device 5 on its plasma side; a heater 10 for maintaining the temperature of the blood in the system at an appropriate value; dripper chambers 11 provided at suitable positions in the blood flow path so as to eliminate air bubbles entrained into the blood therein; an air bubble detecting device 12 for detecting any air bubbles which may in any case have passed the dripper chambers 11 and for preventing them passing into the body of the patient; one or more pressure meters 13 located at appropriate circuit points for sensing the pressure of the blood therein; and a blood return portion 14 which is connected to the body of the patient so as to return said flow of blood thereinto. And the blood plasma constituent treatment circuit 9 which is connected to the plasma side of the blood plasma separator/combiner device 5 comprises: a LDL eliminating device 6 which eliminates LDL from the flow of plasma; a plasma pump 7 for regulating and impelling said flow of plasma; a plasma leakage detecting device 8 for preventing blood corpuscles from becoming mixed in with said plasma; further dripper chambers 11; and further pressure meters 13. Blood plasma is separated from the blood taken out from the circulatory system of the patient by the blood plasma separator/combiner device 5, and is outputted from a plasma output port 5a thereof to the blood plasma constituent treatment circuit 9, while the corpuscles in the blood are retained within the body of said blood plasma separator/combiner device 5. After treatment by the LDL eliminating device 6, this blood is recirculated back to the blood plasma separator/combiner device 5 and is inputted through a plasma input port 5b thereof to be remixed with the blood corpuscles remaining therein, so as to form whole blood which then is returned to the circulatory system of the patient.

Figure 6:
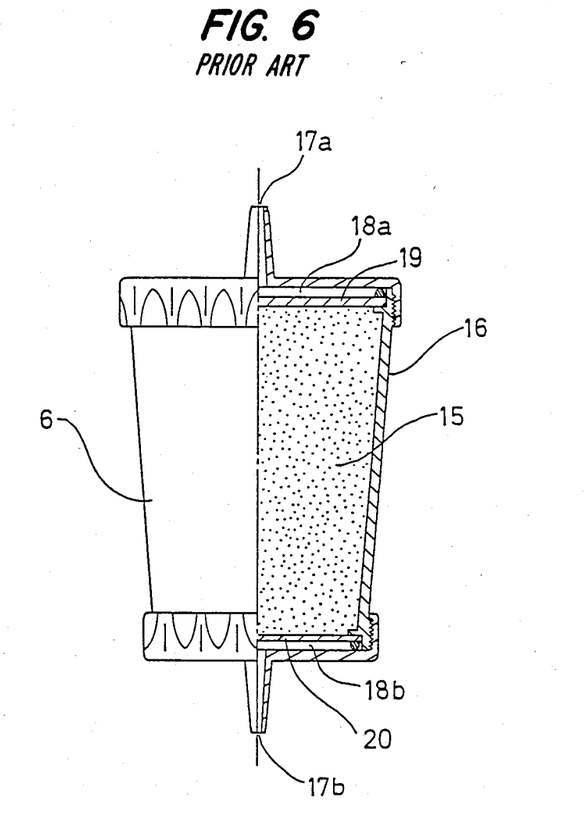
FIG. 6 is a cut away longitudinal cross sectional view of an LDL eliminating device incorporated in the FIG. 5C circuit.

In FIG. 6 of the accompanying drawings, there is shown a cut-away side longitudinal cross sectional view of the LDL eliminating device 6 incorporated in the FIG. 5C circuit. In this figure, the reference numeral 16 denotes the hollow columnar body of the LDL eliminating device 6, which is filled with a quantity 15 formed in very tiny particles of an appropriate per se known substance which can effectively selectively absorb LDL from blood plasma while being non toxic to the human body. Initially, this body 16 of the device 6 is filled with a quantity of physiological saline solution or the like which holds the quantity 15 of the aforesaid tiny particles in suspension. The upper and lower ends of this hollow columnar body 16 of the LDL eliminating device 16 are closed with covers in which are formed an input port 17a and an output port 17b respectively, and at the top end of the quantity 15 of particulate matter contained in said body 16 there is provided a mesh filter 19 (or the like), on the side of which remote from said quantity 15 of particulate matter there is defined an input plenum 18a, while similarly at the bottom end of said quantity 15 of particulate matter there is provided a membrane filter 20 (or the like), on the side of which remote from said quantity 15 of particulate matter there is defined an output plenum 18b. These filters 19 and 20 prevent the tiny particles of the mass 15 of particulate matter from becoming mixed into the plasma flowing back to the body of the patient via the blood plasma separator/combiner device 5. A typical volume for such an LDL eliminating device 6 is about 400 cm$^3$, and in the initial state of the system this device 6 contains about 380 cm$^3$ of the aforesaid dispersion agent of physiological saline solution or the like.

Initially, when the system is first started and blood starts to be taken from the body of the patient, the plasma in this blood, separated out therefrom by the blood plasma separator/combiner device 5, passes through the input port 17a into the input plenum 18a at the top of the LDL eliminating device 6, and pushes downwards and replaces the physiological saline solution contained in the body 15 of said device 6, said physiological saline solution flowing downwards via the output plenum 18b out through the output port 17b to enter the circulatory system of the patient. Thereafter, as the blood plasma comes into contact with the fine particular matter of the particle mass 15, it is purified of LDL, and, as soon as the body 16 of the device 6 is full of plasma and substantially all of the physiological saline solution initially contained therein has been driven out thereof, the purified plasma passes downwards via the output plenum 18b out through the output port 17b to enter the circulatory system of the patient.

As will be clear from the above explanation, when performing blood constituent treatment by the use of such a prior art type of blood constituent treatment apparatus, the interior of the LDL eliminating device 6 becomes filled with blood plasma, and this condition is maintained. Accordingly, only the amount of blood plasma required to fill this device 6 (along with a certain additional amount for filling the intermediate portions of the FIG. 5C circuit) needs to be withdrawn from the body of the patient during the treatment for any considerable time. This may amount to 250 to 400 cm$^3$ or thereabout. Now, there is a fixed physiological limit (called the maximum permissible external circulation volume) to the amount of blood that can safely be withdrawn for any considerable time period from the circulatory system of a patient, and this limit can be low in the case of a severely ill patient. In any case, it is better to have a lower amount of blood so withdrawn, from the medical point of view. On the other hand, in order to increase the treatment capacity of the blood constituent treatment apparatus, it is very desirable to increase its volumetric capacity, and as a result the desired external circulation volume increases. Accordingly, in the case of using a prior art type of blood constituent treatment apparatus as described above, there is a fixed limit to the treatment capacity.

Further, because the physiological saline solution or the like initially filling the blood constituent treatment apparatus is, in the prior art, passed into the body of the patient, the patient's blood is diluted, and an undesirable reduction in the gelatinous osmotic pressure thereof is caused. As in the case of the problem outlined above with respect to the external circulation volume, as long as the prior art type of blood constituent treatment apparatus as described above is utilized, increase of the volumetric capacity thereof inevitably leads to increase in the volume of physiological saline solution thus diluting the blood of the patient, and there is a medical limit to this dilution also; in any case, such dilution should be kept as low as possible. Thus, from this point of view also, there is a fixed limit to the treatment capacity of such a prior art blood constituent treatment apparatus.

And, further, neither of these problems is alleviated, even if a prior art type of circuit with a plurality of treatment devices arranged in parallel, such as exemplarily shown in FIG. 5B, is utilized.

SUMMARY OF THE INVENTION

Accordingly, it is the primary object of the present invention to provide a method for treating blood constituents which overcomes the above identified problems.

It is a further object of the present invention to provide such a method for treating blood constituents which allows the capacity of the apparatus to be maintained or increased without any deleterious effect.

It is a further object of the present invention to provide such a method for treating blood constituents which minimizes the amount of circulatory fluid (whole blood or plasma) that is required to be kept outside the circulatory system of the patient for any considerable time, i.e. the external circulation volume.

It is a further object of the present invention to provide such a method for treating blood constituents which minimizes the total amount of physiological saline solution injected into the circulatory system of the patient.

It is a further object of the present invention to provide such a method for treating blood constituents which has beneficial medical effects.

According to the most general apparatus aspect of the present invention, these and other objects are accomplished by an apparatus for treating circulatory fluid constituents, comprising: (a) a plurality of circulatory fluid treatment devices; (b) individually operable means for selectively individually connecting the input sides of said circulatory fluid treatment devices to inflow of circulatory fluid; (c) individually operable means for selectively individually connecting the output sides of said circulatory fluid treatment devices to outflow of circulatory fluid; and (d) individually operable means for selectively connecting at least some of said output sides of said circulatory fluid treatment devices to at least some of said input sides thereof; and, according to the most general method aspect of the present invention, these and other objects are accomplished by a method for treating circulatory fluid constituents, wherein in the specified order: (a) a selective switching means switches the upstream side of a first circulatory fluid treatment device to receive from a source a flow of circulatory fluid, and switches the downstream side of said first circulatory fluid treatment device to send to a destination said flow of circulatory fluid; and then: (b) said selective switching means, while maintaining said switching of said flow of circulatory fluid to the destination from the downstream side of said first circulatory fluid treatment device, switches the upstream side of said first circulatory fluid treatment device to interrupt communication with said flow of circulatory fluid from said source, further switches the upstream side of said second circulatory fluid treatment device to receive said flow of circulatory fluid from said source, and further switches the downstream side of said second circulatory fluid treatment device to communicate said flow of circulatory fluid to the upstream side of said first circulatory fluid treatment device; and then: (c) said selective switching means, while maintaining said switching of said flow of circulatory fluid from said source into the upstream side of said second circulatory fluid treatment device, switches the downstream side of said first circulatory fluid treatment device to intercept sending flow of circulatory fluid to said destination, and further switches the downstream side of said second circulatory fluid treatment device to send to said destination said flow of circulatory fluid.

According to such a structure and such a method, since only one of said circulatory fluid treatment devices is filled with human circulatory fluid at one time—as will be explained in the following—the amount of circulatory fluid that is required to be kept outside the circulatory system of the patient for any considerable time, i.e. the external circulation volume, is minimized. Further, since as will be explained later only the physiological saline solution initially charged in a single one of said circulatory fluid treatment devices is required to be injected into the circulatory system of the patient, the total amount of such physiological saline solution injected into the circulatory system of the patient is also minimized. Thus, the capacity of the apparatus can be maintained or increased without any deleterious effect.

BRIEF DESCRIPTION OF THE DRAWINGS

The present invention will now be shown and described with reference to the preferred embodiments thereof, and with reference to the illustrative drawings, which, however, are for the purposes of explanation and exemplification only, and are not intended to be limitative of the scope of the present invention in any way. In the drawings, like parts and spaces and so on are denoted by like reference symbols in the various figures thereof; in the description, spatial terms are to be everywhere understood in terms of the relevant figure; and:

FIG. 2, in its three views 2A, 2B, and 2C, shows three stages in the operation of said first preferred embodiment shown in FIG. 1 of the blood constituent treatment apparatus of the present invention;

DESCRIPTION OF THE PREFERRED EMBODIMENTS

Figure 1:
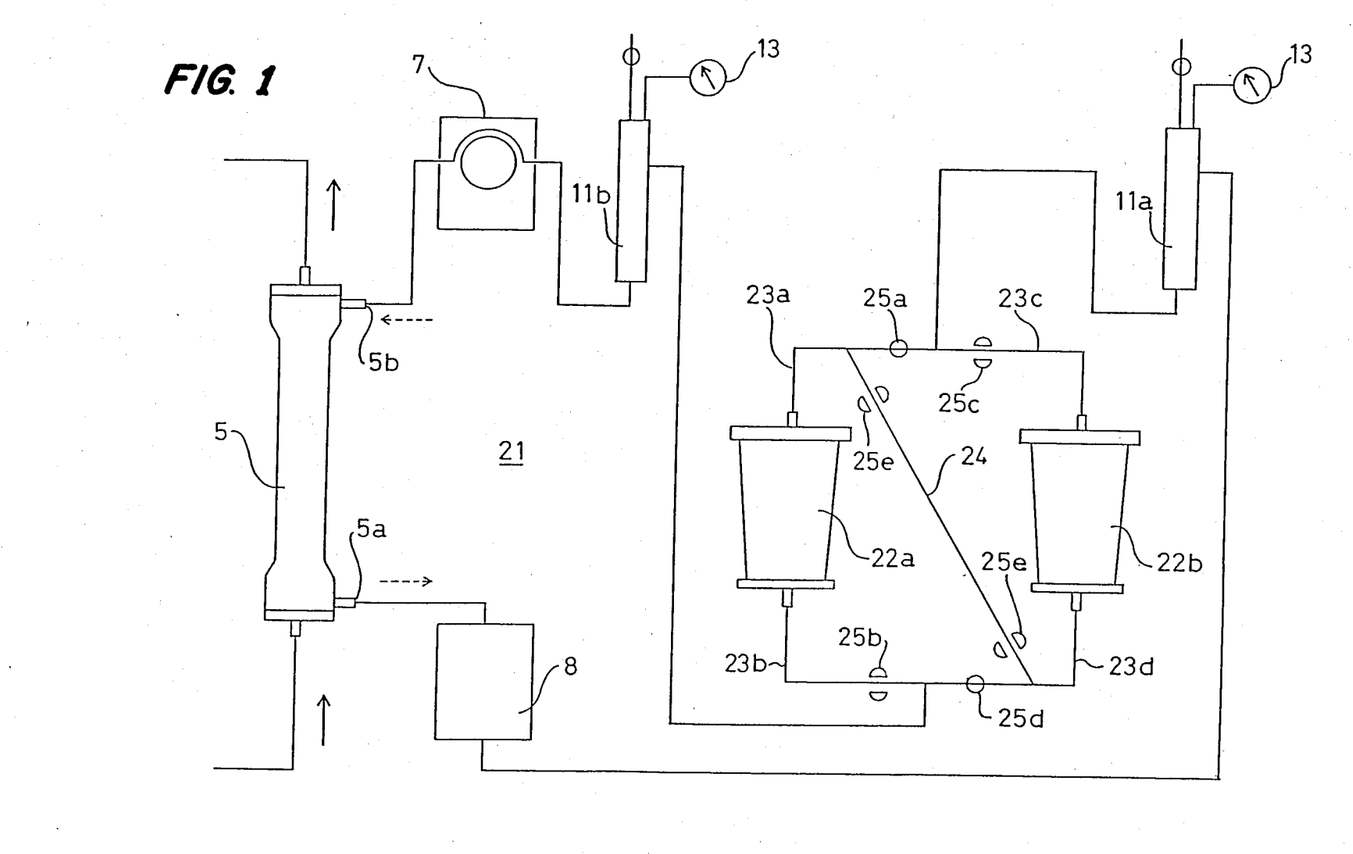
FIG. 1 is a schematic illustration of the first preferred embodiment of the blood constituent treatment apparatus of the present invention, which incorporates two blood constituent treatment devices connected together in a particular manner.

The present invention will now be described with reference to the preferred embodiments thereof, and with reference to the appended drawings. FIG. 1 is a schematic illustration of the first preferred embodiment of the apparatus for treating blood constituents according to the present invention. This exemplary embodiment is an apparatus for removing low density and very low density lipoprotein (hereinafter referred to generically as LDL) from blood, such LDL being as stated previously considered to be the cause of hyperlipemia, as well as of high blood cholesterol level disease, arteriosclerosis, and the like; however, this is not to be considered as limitative of the present invention, which is applicable to many other sorts of blood constituent treatment, as will become understood from what follows hereinafter. In the drawing, the reference numeral 21 designates the shown portion of a circuit incorporated in the apparatus, as a whole, and this circuit portion comprises: a blood plasma separator/combiner device 5 of the type previously described, which provides a flow of plasma separated from the blood of the patient; a plasma pump 7 for regulating and impelling said flow of plasma; a plasma leakage detecting device 8 for preventing blood corpuscles from becoming mixed in with said plasma; dripper chambers 11a and 11b; pressure meters 13; and, further, two LDL eliminating device 22a and 22b, per se of the type previously described with reference to FIG. 6 but typically of about half the volume of the LDL eliminating device 6 of said figure, which are capable of eliminating LDL from the flow of plasma passing through them. The upper or upstream side of the first LDL eliminating device 22a is connected to the downstream side of the first dripper 11a by inflow conduit means, such as a conduit 23a, in which switching means, such as an ON/OFF switching device 25a such as a forceps, a pinch valve, a partitioning valve, a cock, or the like is fitted; and the lower or downstream side of said first LDL eliminating device 22a is connected to the upstream side of the second dripper 11b by an outflow conduit means, such as a conduit 23b in which a similar ON/OFF switching device 25b is fitted. Similarly, the upper or upstream side of the second LDL eliminating device 22b is connected to said downstream side of said first dripper 11a by a conduit 23c in which a similar ON/OFF switching device 25c is fitted; and the lower or downstream side of said second LDL eliminating device 22b is connected to said upstream side of said second dripper 11b by a conduit 23d, in which a similar ON/OFF switching device 25d is fitted. Also, particularly according to the gist of the present invention, the upper or upstream side of the first LDL eliminating device 22a is connected to the downstream side of the second LDL eliminating device 22b by an interconnecting conduit means, such as a transfer conduit 24, in which a pair of similar ON/OFF switching devices 25e are fitted. Blood plasma is separated from the blood taken out from the circulatory system of the patient by the blood plasma separator/combiner device 5, and is outputted from a plasma output port 5a thereof to the blood plasma constituent treatment circuit 21, while the corpuscles in the blood are retained within the body of said blood plasma separator/combiner device 5. After treatment by the LDL eliminating device 22a, 22b, this blood is recirculated back to the blood plasma separator/combiner device 5 and is inputted through a plasma input port 5b thereof to be remixed with the blood corpuscles remaining therein, so as to form whole blood which then is returned to the circulatory system of the patient.

Figure 2A:
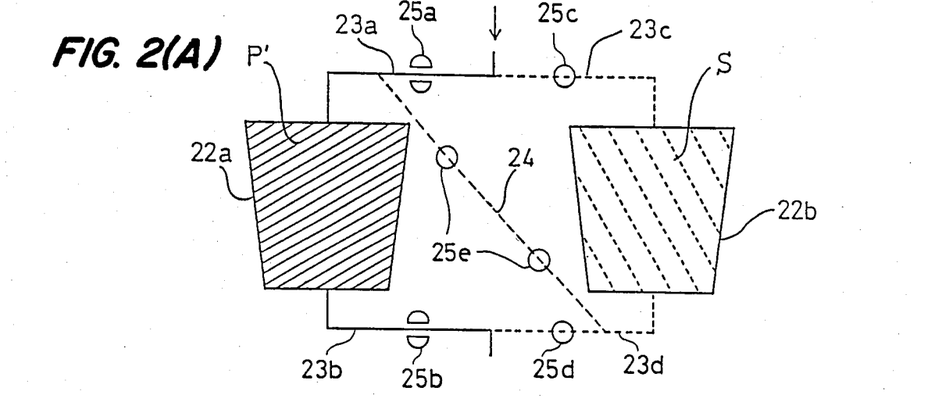

This first preferred embodiment of the apparatus for treating blood constituents according to the present invention functions as follows, according to the first preferred method embodiment of the present invention. At the start of operation, the ON/OFF switching devices 25a and 25b are ON (i.e., open), while the ON/OFF switching devices 25c, 25d, and 25e are all OFF (i.e., closed), and the first and second LDL eliminating devices 22a and 22b are filled with physiological saline solution or the like. This establishes a circuit as shown in FIG. 2A.

In this state of the apparatus, the blood plasma, which as explained before with relation to the prior art is separated by the blood plasma separator/combiner device 5 from the blood taken out from the body of the patient, is directed into the top side of the first LDL eliminating device 22a, and as explained above initially the quantity of physiological saline solution held in said first LDL eliminating device 22a is injected into the circulatory system of the patient as the plasma fills said first LDL eliminating device 22a and displaces said physiological saline solution, after which the plasma commences to be treated by being purified of LDL in said device 22a. However, this quantity of physiological saline solution is about half as much as was thus injected in the case of the prior art mentioned heretofore. Also at this time the flow of plasma is completely intercepted from passing into the second LDL eliminating device 22b by the action of the closed ON/OFF switching devices 25c, 25d, and 25e. This state of the apparatus, in which the first LDL eliminating device 22a is filled with a mass P' of plasma while the second LDL eliminating device 22b is still filled with a mass S of physiological saline solution, is the one shown in FIG. 2A.

Figure 2B:
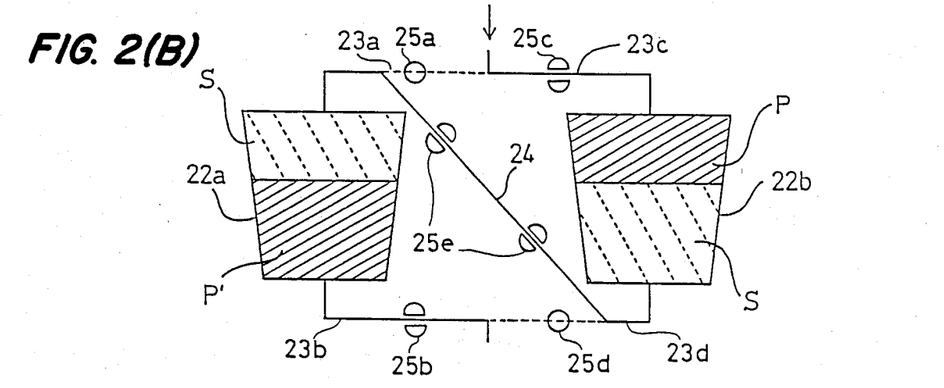

If and when the capacity of this first LDL eliminating device 22a for purifying the blood plasma of LDL becomes deteriorated, then the ON/OFF switching device 25b being left in an ON (open) condition, the ON/OFF switching device 25a is put into the OFF (closed) condition by the operator or by an automatic switching means, and the ON/OFF switching device 25d is left in the OFF (closed condition, while on the other hand the ON/OFF switching devices 25c and 25e are put into the ON (open) condition, and thereby a circuit including the transfer conduit 24 is established, as shown in FIG. 2B, in which the first and second LDL eliminating devices 22a and 22b are connected in series, with the second such device 22b upstream of the first device 22a.

In this state of the apparatus, a mass P of blood plasma, which now is directed into the top side of the second LDL eliminating device 22b, starts to displace the quantity S of physiological saline solution held in said second LDL eliminating device 22b and to drive it out of the outlet of said device 22b. This physiological saline solution mass S passes down along the transfer conduit 24 to enter into the inlet of the first LDL eliminating device 22a, and displaces the plasma mass P' still retained therein, said plasma mass P' being injected into the circulatory system of the patient as the physiological saline solution mass S fills said first LDL eliminating device 22a. Thereby, the physiological saline solution mass S initially filling the second LDL eliminating device 22b is not injected into the circulatory system of the patient, but on the contrary serves the useful function of pushing out the plasma mass P' remaining in the first LDL eliminating device 22a into said patient's circulatory system.

Figure 2C:
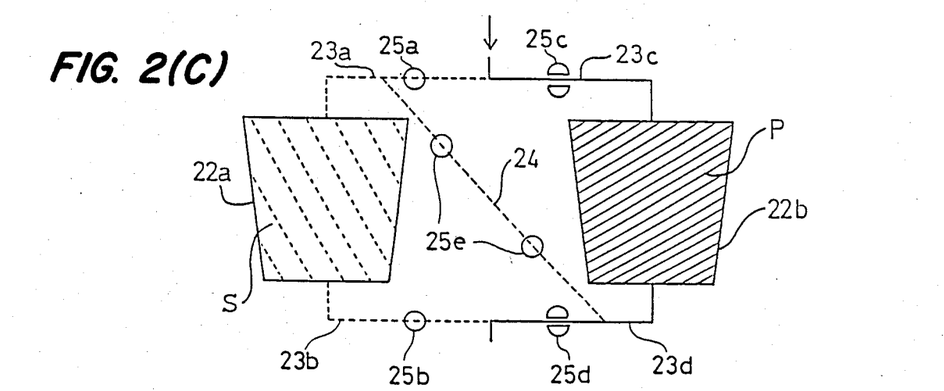

Now, because the first and second LDL eliminating devices 22a and 22b are constructed to have substantially the same volume, at the time point when substantially all of the mass S of physiological saline solution held in the second LDL eliminating device 22b has thus been driven out of it by the entering plasma into the second LDL eliminating device 22b, substantially all of the plasma mass P' remaining in said first LDL eliminating device 22a will have been driven out of it into the circulatory system of the patient. When this is judged to have happened, the ON/OFF switching device 25a is kept in its OFF (closed) condition, the ON/OFF switching device 25c is kept in its ON (open) condition, the ON/OFF switching devices 25b and 25e are put into their OFF (closed) condition, while the ON/OFF switching device 25d is put into its ON (open) condition, and this establishes a circuit as shown in FIG. 2C, in which the blood plasma which is being separated by the blood plasma separator/combiner device 5 from the blood taken out from the body of the patient is directed into the top side of the second LDL eliminating device 22b and is treated by being purified of LDL in said device 22b. And at this time the flow of plasma is completely intercepted from passing into the first LDL eliminating device 22a by the action of the closed ON/OFF switching devices 25a, 25b, and 25e. This state of the apparatus, in which the first LDL eliminating device 22a is filled with the mass S of physiological saline solution initially held in the second LDL eliminating device 22b, while the second LDL eliminating device 22b is filled with a mass P of plasma, is the one shown in FIG. 2C.

Thus it is seen that, according to this first preferred embodiment of the apparatus and the method of the present invention, due to the division of the LDL elimination capacity into two portions which are used in succession, the amount of blood that is required to be kept outside the circulatory system of the patient for any considerable time, i.e. the external circulation volume, is about half of what it was in the prior art detailed above. Further, the total amount of physiological saline solution injected into the circulatory system of the patient is about half of what it was in the case of the prior art. Thereby good medical benefits are obtained, and the treatment capacity of the apparatus can be increased without any deleterious effects arising therefrom. Also, because the switched state of the ON/OFF switching devices can be quickly altered, it is possible to minimize the treatment time for the patient.

Figure 3:
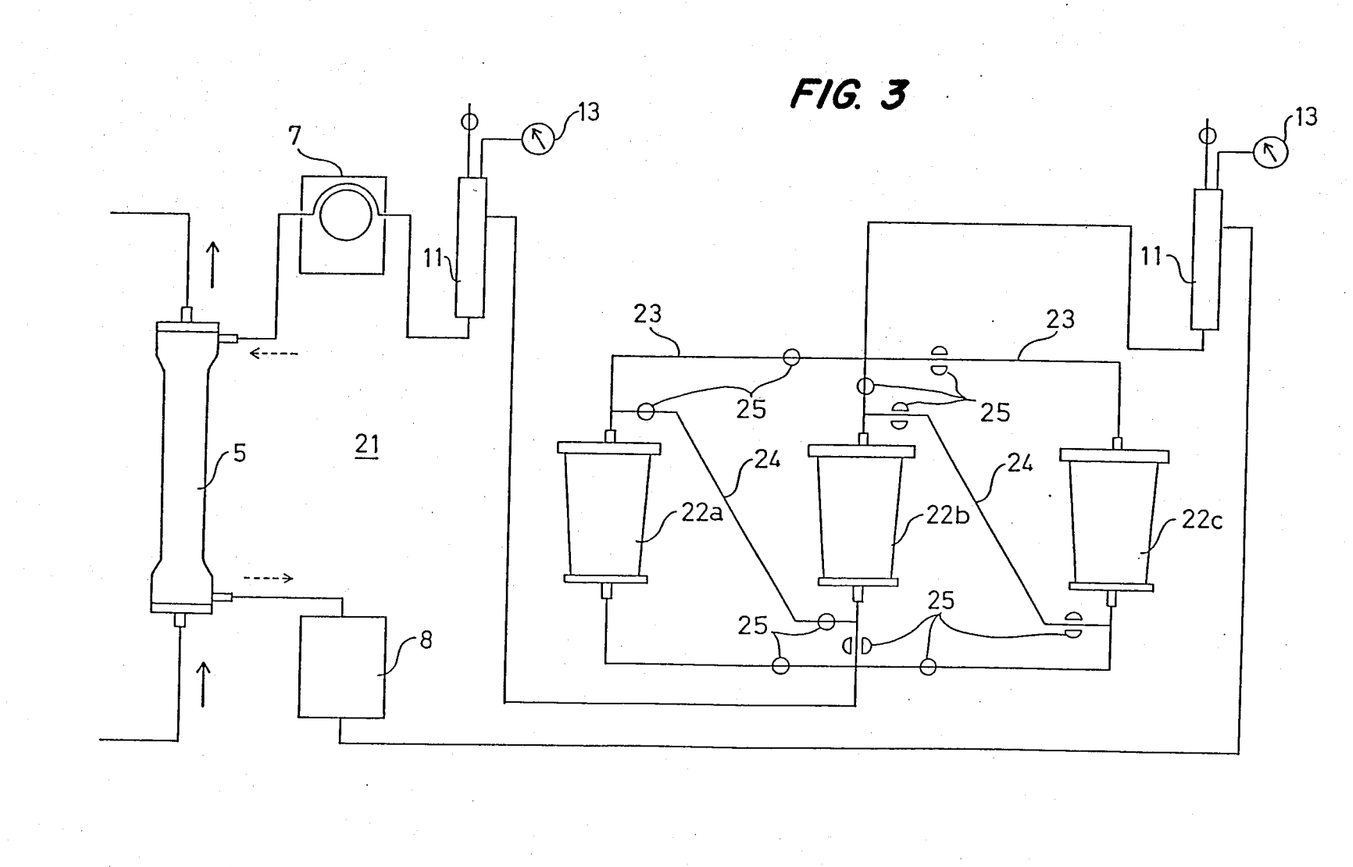
FIG. 3 is a schematic illustration of the second preferred embodiment of the blood constituent treatment apparatus of the present invention, which incorporates three such blood constituent treatment devices connected together in another particular manner.

In the above described first preferred embodiments, the total treatment capacity for LDL elimination was divided into two parts between the first and the second LDL eliminating devices 22a and 22b, but this is not intended to be limitative of the present invention: in fact, more fine division is possible. FIG. 3 shows the second preferred embodiment of the blood constituent treatment apparatus of the present invention for practicing the second preferred method embodiment, which incorporates three such blood constituent treatment devices 22a, 22b, and 22c connected together in a manner analogous to that shown and described with respect to the first preferred embodiment. The way in which this second preferred embodiment functions will be clear to one of ordinary skill in the relevant art without undue experimentation, based upon the disclosure given herein with respect to the first preferred embodiment; hence, the second preferred embodiment will not be descanted upon at length, in the interests of brevity of explanation. In this second preferred embodiment, the volumetric capacities of each of the three LDL eliminating devices 22a, 22b, and 22c can be made to be a third of that of the device of FIG. 6 according to the prior art, and hence the amount of plasma that is required to be kept outside the circulatory system of the patient for any considerable time, i.e. the external circulation volume, is yet smaller than in the case of the first preferred embodiment. Thus, correspondingly, the total amount of physiological saline solution injected into the circulatory system of the patient is even less than what is was in the case of the first preferred embodiment.

Figure 4:
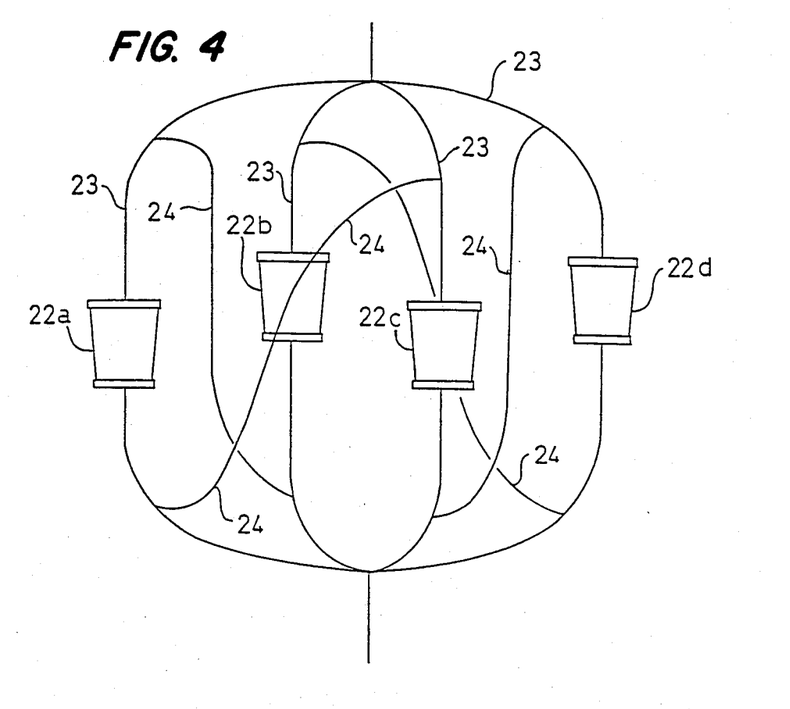
FIG. 4 is a partial schematic illustration of the third preferred embodiment of the blood constituent treatment apparatus of the present invention, which incorporates four such blood constituent treatment devices connected together in yet another particular manner.

Further, it is possible to further subdivide the LDL eliminating capacity. FIG. 4 shows the essential parts of the third preferred embodiment of the blood constituent treatment apparatus of the present invention for practicing the third preferred method embodiment, which incorporates four such blood constituent treatment devices 22a, 22b, 22c, and 22d connected together in a manner analogous to that shown and described with respect to the first and second preferred embodiments. The various switching valves utilized in this third preferred embodiment are omitted, since the arrangement thereof is complicated but is clear to one of ordinary skill in the relevant art without undue experimentation, based upon the disclosure given herein with respect to the first and second preferred embodiments, as is the method of operation of this third preferred embodiment; hence, these matters will not be particularly discussed herein. In this third preferred embodiment, the volumetric capacities of each of the four LDL eliminating devices 22a, 22b, 22c, and 22d can be made to be a quarter of that of the device of FIG. 6 according to the prior art, and hence the amount of plasma that is required to be kept outside the circulatory system of the patient for any considerable time, i.e. the external circulation volume, is yet smaller than in the case of the first and second preferred embodiments; and, correspondingly, the total amount of physiological saline solution injected into the circulatory system of the patient is even less than what it was in the case of said first and second preferred embodiments. Additionally, if the transfer conduits are appropriately provided in sufficient number, it is possible to commence treatment using any of the four LDL eliminating devices 22a, 22b, 22c, and 22d, and to operate said four LDL eliminating devices 22a, 22b, 22c, and 22d in any desired sequential order.

The present invention is not to be considered as being limited to the elimination of LDL from blood plasma, but can be applied to the elimination of many types of noxious substances from blood by employing adsorptive substances, as well as to aritificial metabolism employing immobilized enzymes or the like, and further to blood treatment with drug additives. Further, the present invention is not to be considered as limited to the treatment of blood plasma only, but also may be applied to the treatment of whole blood. Accordingly, although the present invention has been shown and described with reference to the preferred embodiments thereof, and in terms of the illustrative drawings, it should not be considered as being limited thereby, since many alterations could be made in the perhaps purely fortuitous details thereof, but as being defined solely by the scope of the appended claims, which follow.

What is claimed is:

1. A method for treating circulatory fluid constituents, wherein in the specified order:
   (a) a selective switching means switches the upstream side of a first circulatory fluid treatment device to receive from a source a flow of circulatory fluid, and switches the downstream side of said first circulatory fluid treatment device to send to a destination said flow of circulatory fluid; and then:
   (b) said selective switching means, while maintaining said switching of said flow of circulatory fluid to the destination from the downstream side of said first circulatory fluid treatment device, switches the upstream side of said first circulatory fluid treatment device to interrupt communication with said flow of circulatory fluid from said source, further switches the upstream side of said second circulatory fluid treatment device to receive said flow of circulatory fluid from said source, and further switches the downstream side of said second circulatory fluid treatment device to communicate said flow of circulatory fluid to the upstream side of said first circulatory fluid treatment device; and then:
   (c) said selective switching means, while maintaining said switching of said flow of circulatory fluid from said source into the upstream side of said second circulatory fluid treatment device, switches the downstream side of said first circulatory fluid treatment device to intercept sending flow of circulatory fluid to said destination, and further switches the downstream side of said second circulatory fluid treatment device to send to said destination said flow of circulatory fluid.

2. A method according to claim 1, wherein during step (b) a quantity of fluid initially filling said second circulatory fluid treatment device is discharged therefrom into said first circulatory fluid switching device, while a quantity of circulatory fluid remaining in and filling said first circulatory fluid treatment device is discharged therefrom to said destination.

* * * * *